(12) United States Patent
Caputi et al.

(10) Patent No.: US 8,686,215 B2
(45) Date of Patent: Apr. 1, 2014

(54) ABSORBENT ARTICLES COMPRISING AN ODOUR CONTROL SYSTEM

(75) Inventors: Mariangela Caputi, Pescara (IT);
Luigia D'Ercole, Montesilvano (IT);
Remo Bellucci, Spoltore (IT); Nicola D'Alesio, Canosa Sannita (IT); Jessica Marcuccitti, Chieti (IT); Adelia Alessandra Tordone, Pescara (IT)

(73) Assignee: The Procter amd Gamble Company, Cincinnati, OH (US)

( * ) Notice: Subject to any disclaimer, the term of this patent is extended or adjusted under 35 U.S.C. 154(b) by 308 days.

(21) Appl. No.: 12/817,371

(22) Filed: Jun. 17, 2010

(65) Prior Publication Data
US 2010/0324512 A1 Dec. 23, 2010

(30) Foreign Application Priority Data
Jun. 18, 2009 (EP) .................................. 09163106

(51) Int. Cl.
*A61F 13/15* (2006.01)
(52) U.S. Cl.
USPC ............................ 604/359; 604/361; 604/367
(58) Field of Classification Search
USPC .......................................... 604/359, 361, 367
See application file for complete search history.

(56) References Cited

U.S. PATENT DOCUMENTS

| | | | |
|---|---|---|---|
| 4,904,307 A | 2/1990 | Ammeraal et al. | |
| 5,094,761 A | 3/1992 | Trinh et al. | |
| 5,135,747 A | 8/1992 | Faryniarz et al. | |
| 5,403,828 A | 4/1995 | Lewis et al. | |
| 5,635,238 A | 6/1997 | Trinh et al. | |
| 5,660,845 A | 8/1997 | Trinh et al. | |
| 5,714,445 A | 2/1998 | Trinh et al. | |
| 5,861,144 A | 1/1999 | Peterson et al. | |
| 6,110,449 A | 8/2000 | Bacon et al. | |
| 6,287,603 B1 | 9/2001 | Prasad et al. | |
| 6,893,647 B1 | 5/2005 | Malton et al. | |
| 7,033,645 B2 | 4/2006 | Gatto et al. | |
| 7,041,337 B2 | 5/2006 | Heltovics et al. | |
| 7,208,462 B2 | 4/2007 | Heltovics et al. | |
| 7,208,463 B2 | 4/2007 | Heltovics et al. | |
| 7,208,464 B2 | 4/2007 | Heltovics et al. | |
| 7,208,465 B2 | 4/2007 | Heltovics et al. | |
| 7,407,650 B2 | 8/2008 | Heltovics et al. | |
| 7,413,731 B2 | 8/2008 | Heltovics et al. | |
| 7,473,817 B1 * | 1/2009 | Tanaka et al. | 604/358 |
| 2003/0060379 A1 | 3/2003 | Souter et al. | |
| 2003/0069165 A1 | 4/2003 | Malton et al. | |

(Continued)

FOREIGN PATENT DOCUMENTS

| | | |
|---|---|---|
| EP | 392607 | 10/1990 |
| EP | 392608 A1 | 10/1990 |

(Continued)

OTHER PUBLICATIONS

PCT Search Report, International Application No. PCT/US2010/038952, mail date Aug. 25, 2010, 12 pages.

*Primary Examiner* — Jacqueline F. Stephens
(74) *Attorney, Agent, or Firm* — Andres E. Velarde; Megan C. Hymore; Amanda T. Barry

(57) ABSTRACT

An absorbent article comprising an odor control material comprising at least one inclusion complex of cyclodextrin with an organic compound which is dispersed in a matrix comprising a polysiloxane oil.

13 Claims, 1 Drawing Sheet

(56) References Cited

U.S. PATENT DOCUMENTS

| | | |
|---|---|---|
| 2004/0122387 A1 | 6/2004 | Long et al. |
| 2005/0089540 A1* | 4/2005 | Uchiyama et al. ............ 424/401 |
| 2006/0137958 A1 | 6/2006 | Bogdanovic |
| 2006/0243322 A1 | 11/2006 | Heltovics et al. |
| 2008/0071238 A1 | 3/2008 | Sierri et al. |
| 2008/0213191 A1 | 9/2008 | Scavone et al. |
| 2008/0213204 A1 | 9/2008 | Scavone et al. |
| 2008/0215023 A1 | 9/2008 | Scavone et al. |
| 2009/0105676 A1 | 4/2009 | Brusk et al. |
| 2009/0214446 A1 | 8/2009 | Strassburger |

FOREIGN PATENT DOCUMENTS

| | | |
|---|---|---|
| EP | 1024785 A1 | 8/2000 |
| JP | 10263062 A1 | 10/1998 |
| JP | 11209784 A1 | 8/1999 |
| JP | 2001316219 A | 11/2001 |
| WO | 9856340 A1 | 12/1998 |

* cited by examiner

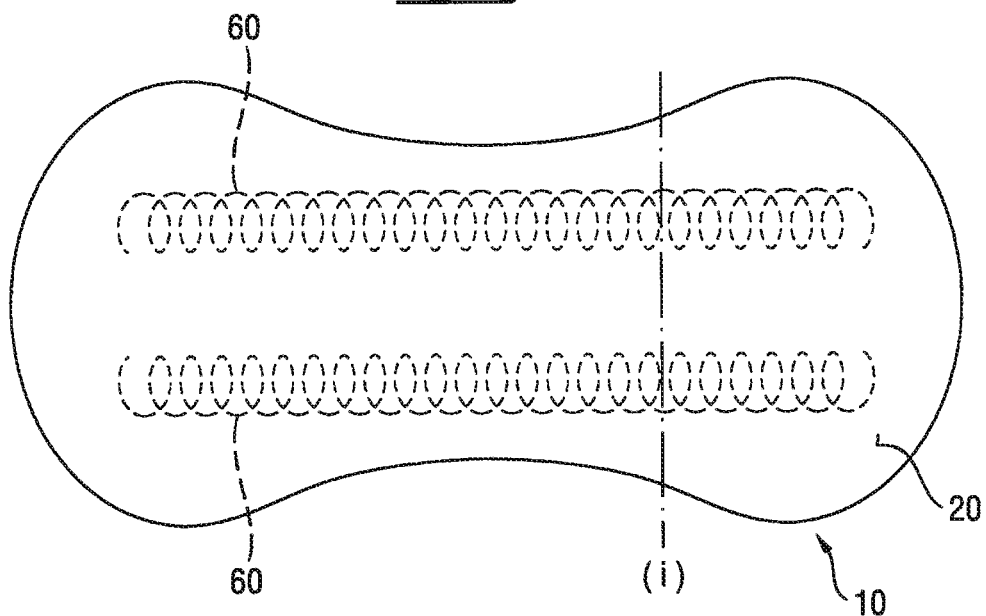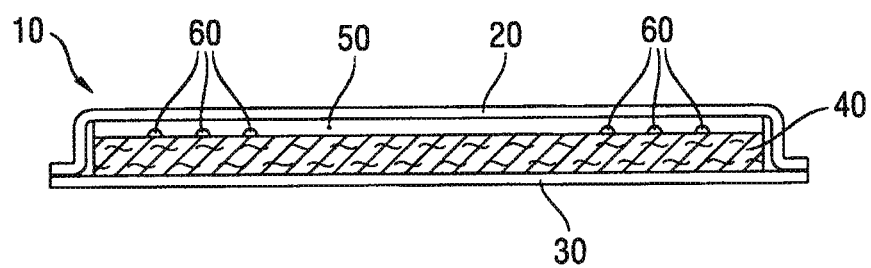

ABSORBENT ARTICLES COMPRISING AN ODOUR CONTROL SYSTEM

FIELD OF THE INVENTION

The present invention relates to absorbent articles for bodily fluids which include an odour control system which is activated only when needed by the moisture contained within the bodily fluids.

BACKGROUND OF THE INVENTION

Absorbent articles for personal hygiene are known in the art. Typical examples include sanitary napkins, panty liners, tampons, inter labial articles, adult incontinence articles, and baby diapers. Such articles are commonly used to absorb and retain bodily fluids and other exudates excreted by the human body. Typically, such exudates are perceived as malodourous and offensive. Therefore, methods and materials for controlling and reducing malodours in absorbent articles have been developed. Fragrance materials have been widely used for this purpose in absorbent articles, as well as ingredients such as silica or zeolites which are able to entrap some of the malodour generating molecules.

Other materials which are useful to improve the odour perception of absorbent articles are compounds that may or many not have a pleasant odour per se but which are able to improve the odour perception of the composition or article to which they are associated. Such materials may act, for example, by modifying how certain nose receptors perceive malodours, or by acting on the malodourous substance by chemical reaction, or complexation, or absorption/adsorption, for example.

In the present application the term "odour control material" includes any material which, as all those mentioned above, is able to improve the perceived odour of the absorbent article before, during, and/or after its use.

A large class of ingredients which is desirable to use as components of an odour control material for use in absorbent articles is that of organic compounds. In the context of the present application for "organic compounds" it is intended organic molecules which, introduced within an absorbent article, are capable to provide an improvement of the perceived odour from the article. Differently from inorganic components such silica, carbon black and zeolites which physically entrap malodours, organic compounds which are active on the odour perception of the user of the absorbent article, are directly active in modifying the odour of an absorbent article at any stage of use for example by providing a scent, by directly or indirectly reacting with malodorous substances ("indirectly" it is intended for example when an organic compound has an antimicrobial effect on microbes which generate malodorous substances) or by modifying the perception of malodours from the nose receptors.

Most organic compounds usable in odour control materials are volatile and tend to evaporate to some extent so that their amount in a commercial absorbent article is difficult to control. After the absorbent article is manufactured, the organic compounds start evaporating and, depending on the time and conditions of storage before its usage, a more or less large part of the odour control material will be evaporated and therefore not effective anymore.

Sealing the articles solves the problem only in part because a sealing which is compatible with the cost of such absorbent articles is usually not perfect and anyway a large amount of volatile odour control materials is also lost during the usage of the absorbent article also triggered by the body heat.

Odour control materials are instead most needed at the time when the absorbent article is loaded with bodily fluids, i.e. in the final period of its usage and during its replacement.

The most highly volatile odour control materials tend to evaporate in the first minutes of use of the article providing, for example, a pleasant feel during the process of wearing the article but no other benefits when, later, the article is loaded with malodorous bodily fluids.

In order to preserve volatile compounds for longer a successful route is to incorporate the volatile organic compounds into inclusion complexes of cyclodextrins (alpha cyclodextrins and/or beta cyclodextrins are examples of cyclodextrines which can be used herein). Examples of such complexes are described in U.S. Pat. No. 5,580,851 and in WO2008/104960 but any inclusion complex of a cyclodextrin with an organic compound can be used in the present invention. These complexes are very effective because they retain the odour control active and release it when they are wetted by the bodily fluids.

Inclusion complexes of cyclodextrin molecules are generally in the form of a fine particulate material which is commonly produced via spray drying of a solution containing the cyclodextrin and the organic compounds. It is believed that the cyclodextrins form the inclusion complex with the organic compounds and, when spray dried they prevent the organic compound from evaporating due to the chemical bonds formed with the complexed compound. When the material is wetted these bonds are weakened and the organic compound slowly released. Particulate materials are sometime troublesome to handle in certain manufacturing plants because of safety regulations which impose a very careful handling of fine powders, especially of organic compounds as it is the case with the inclusion complexes of beta cyclodextrin.

Moreover the natural air humidity and the humidity of the absorbent article may trigger the release of the complexed organic compound earlier than desired.

It is therefore desirable to provide articles comprising such inclusion complexes in a form which can be easily incorporated in such articles and which is protected from humidity.

SUMMARY OF THE INVENTION

The present invention relates to an absorbent article comprising an odour control material, said odour control material comprising at least one inclusion complex of cyclodextrin with an organic molecule which is dispersed in a matrix comprising a polysiloxane oil.

BRIEF DESCRIPTION OF THE DRAWINGS

FIG. 1 is a plan view of an absorbent article.
FIG. 1b shows a cross-section of the absorbent article of FIG. 1 along the line indicated by (i).

DETAILED DESCRIPTION OF THE INVENTION

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings and perspiration pads, incontinence pads, as well as absorbent articles for feminine hygiene like sanitary napkins, panty liners, tampons, interlabial devices or the like. Absorbent articles suitable for use in the present invention include any type of structures, from a single absorbent layer to more complex multi layer structures. Certain absorbent articles include a fluid pervious topsheet, a backsheet, which may be fluid impervious and/or may be water vapour and/or gas pervious, and an absorbent element comprised there between, often also referred to as "absorbent core" or simply "core".

The term "use", as used herein, refers to the period of time that starts when the absorbent article is actually put in contact with the anatomy of a wearer.

By "body fluid" it is meant herein any fluid produced by human body including, but not limited to, perspiration, urine, menstrual fluids, vaginal secretions and the like.

The present invention relates to an absorbent article comprising an odour control material, said odour control material comprising at least one inclusion complex of cyclodextrin with an organic molecule which is dispersed in a matrix comprising a polysiloxane oil.

The absorbent article of the present invention can be any kind of absorbent article for personal hygiene known in the art, as described above, particularly an absorbent article for feminine hygiene, and typically comprises a liquid permeable topsheet, a backsheet, and an absorbent element therebetween. Each of these elements, as well as any other optional layer present in the absorbent article, has a body facing side or wearer facing side, and a garment facing side or outer facing side, which correspond to the side facing respectively the body and the garment of the wearer during use of the product. As well known in the art, other additional layers of material can also be present like a secondary topsheet and or acquisition layers which might be present between the topsheet and the absorbent element and in general are used to improve distribution and prevent return on the topsheet of the bodily fluids.

As it is known in the art, topsheets may be manufactured from a wide range of materials which include, but are not limited to, woven and nonwoven materials; polymeric materials such as apertured formed thermoplastic films, apertured plastic films, and hydroformed thermoplastic films; porous foams; reticulated foams; reticulated thermoplastic films; and thermoplastic scrims. A topsheet is typically a specific separate element in the absorbent article of the present invention, comprising one or more layers; however, in an absorbent article according to the present invention the topsheet is meant to correspond to the layer or element which in use goes in direct contact with the user's body, for example, the topsheet can be the topmost layer of the absorbent element, being substantially part of the absorbent element itself.

The absorbent element can be any absorbent member which is generally compressible, conformable, non-irritating to the wearer's skin, and capable of absorbing and retaining liquids such as urine and other certain body exudates. The absorbent element may be manufactured in a wide variety of sizes and shapes (e.g., rectangular, hourglass, T shaped, asymmetric, etc.) and from a wide variety of liquid-absorbent materials commonly used in disposable pull on garments and other absorbent articles such as comminuted wood pulp which is generally referred to as airfelt. Examples of other suitable absorbent materials include creped cellulose wadding; meltblown polymers including coform; chemically stiffened, modified or cross linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent element may vary (e.g., the absorbent element may have varying caliper zones, a hydrophilic gradient, a superabsorbent gradient, or lower average density and lower average basis weight acquisition zones; or may include one or more layers or structures). Further, the size and absorbent capacity of the absorbent element may also be varied to accommodate wearers ranging from infants through adults. However, the total absorbent capacity of the absorbent element should be compatible with the design loading and the intended use of the disposable article.

The absorbent element may include other optional components. One such optional component is the core wrap, i.e., a material, typically but not always a nonwoven material, which either partially or totally surrounds the absorbent element. Suitable core wrap materials include, but are not limited to, cellulose, hydrophilically modified nonwoven materials, perforated films and combinations thereof.

The backsheet may be impervious to liquids (e.g., urine or menses) and can be manufactured from a thin plastic film. In an alternative embodiment the backsheet permits vapours to escape from the disposable absorbent article; for example, a microporous polyethylene film or a non woven can be used as backsheet. One suitable material for the backsheet of the absorbent article of the present invention can be a liquid impervious thermoplastic film having a thickness of from about 0.012 mm to about 0.051 mm, for example including polyethylene or polypropylene. The backsheet may have a basis weight of from about 5 g/m² to about 35 g/m². However, it should be noted that other flexible liquid impervious materials may be alternatively used as the backsheet. Herein, "flexible" refers to materials which are compliant and which will readily conform to the general shape and contours of the wearer's body. The backsheet is typically positioned adjacent the outer-facing side of the absorbent core, and can be joined thereto by any suitable attachment means known in the art. For example, the backsheet may be secured to the absorbent core by a uniform continuous layer of adhesive, a patterned layer of adhesive, or an array of separate lines, spirals, or spots of adhesive.

When the absorbent article of the present invention is an article for feminine hygiene like a sanitary napkin, a panty liner, or an article for light incontinence, it is typically used by being adhered to the crotch portion of an undergarment by means of an attachment means, typically a layer of pressure sensitive adhesive, usually referred to as the panty fastening adhesive, provided onto the garment facing side of the backsheet. Before use, the panty fastening adhesive is protected by a release layer releasably adhered thereto, which is removed by the user to expose the adhesive when the article is to be applied to the undergarment. As it is known in the art, the release layer may be for example a sheet of siliconized paper, or a wrapper sheet, typically made of a polymeric film, which may also provide a releasable unitary wrapper for the article.

The absorbent articles of the present invention comprise an odour control material, said odour control material comprising at least one inclusion complex of cyclodextrin with an organic compound which is dispersed in a matrix comprising a polysiloxane oil.

Organic Compounds

As mentioned in the "Background of the invention" section, a large class of ingredients which is desirable to use as components of an odour control material for use in absorbent articles is that of organic compounds. In particular of organic compounds which are active on the perception of odours by the user of the absorbent article.

Such compounds include all fragrance ingredients (as they are known to those skilled in the art of perfumes) and also all those organic compounds which are not traditionally considered "fragrance materials" but which are directly active in modifying the odour of an absorbent article at any stage of use for example by providing a scent, by directly or indirectly reacting with malodorous substances ("indirectly" it is intended for example when an organic compound has an antimicrobial effect on microbes which generate malodorous substances) or by modifying the perception of malodours from the nose receptors. Lists of organic compounds which are suitable for use herein especially as non traditional fragrance materials are those mentioned in patent applications EP1886698, EP1842564 and WO2008/104960 all from The Procter & Gamble Company.

In term of reactive compounds those reacting with ammonia are very effective. Ammonia is in fact one component of body fluid malodour. For example ammonia is present in high amounts in products used for urine absorption due to degradation of urea. Ammonia and its derivatives can react with aldehydes to form imines (according to the so-called Schiff base reaction).

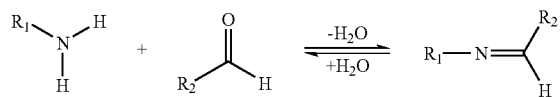

This reaction is catalyzed by enzymes and/or by a slightly acidic pH 4 to 5. The moderate acid requirement is necessary to allow protonation of the hydroxyl intermediate to allow water to leave.

Many aldehydes capable of imine reaction have an unpleasant and/or too intense odour that can be disturbing to human nose and/or they are very volatile and so not stable on the product. Therefore, in most embodiments, selected aldehydes for controlling malodour are used. Examples of suitable aldehydes for controlling malodour are those aldehydes that are able to react with amine compounds according to Schiff base reaction and have not unpleasant odour. Suitable aldehydes include hexyl cinnamic aldehyde, alpha-amylcinnamic aldehyde, p-anisaldehyde, 4-Formyl-2-methoxyphenyl 2-methylpropanoate, benzaldehyde, cinnamic aldehyde, cuminic aldehyde, decanal, p-t-butyl-alpha-methyldihydrocinnamaldehyde, 4-hydroxy-3-methoxycinnamaldehyde, 2-phenyl-3-(2-furyl)prop-2-enal, vanillin isobutyrate, ethyl vanillin acetate, vanillin acetate, cyclamen aldehyde, heptanal, lauryl aldehyde, nonanal, octanal, phenylacetaldehyde, phenyl propyl aldehyde, vanillin, salycil aldehyde, cytral, 2,4-dihydroxy-3-methylbenzaldehyde, 2-hydroxy-4-methylbenzaldehyde, 5-methyl salicylic aldehydes, 4-nitrobenzaldehyde, o-nitrobenzaldehyde, 5-ethyl-2-thiophenecarbaldehyde, 5-methyl-2-thiophenecarboxaldehyde, 2-thiophenecarbaldehyde, asaronaldehyde, 5-(hydroxymethyl)-2-furaldehyde, 2-benzofurancarboxaldehyde, 2,3,4-trimethoxybenzaldehyde, protocatechualdehyde, heliotropine, 4-ethoxy-3-methoxy benzaldehyde, 3,4,5-trimethoxybenzaldehyde, 3-hydroxybenzaldehyde, o-methoxycinnamaldehyde, 3,5-dimethoxy-4-hydroxycinnamaldehyde, 2,8-dithianon-4-3n-4-carboxaldehyde, sorbinaldehyde, 2,4-heptadienal, 2,4-decadienal, 2,4-nonadienal, 2,4-nonadienal, (E,E)-, 2,4-octadien-1-a1, 2,4-octadienal, 2,4-dodecadienal, 2,4-undecadienal, 2,4-tridecadien-1-al, 2-trans-4-cis-7-cis-tridecatrienal, piperonylidene propionaldehyde, 2-methyl-3-(2-furyl)acrolein, 2,4-pentadienal, 2-furfurylidene butyraldehyde, 3-(2-furyl)acrolein, pyruvaldehyde, ethanedial and mixtures thereof.

In another embodiment aldehydes may be selected from hexyl cinnamic aldehyde, decanal, 4-Formyl-2-methoxyphenyl 2-methylpropanoate, 4-hydroxy-3-methoxycinnamaldehyde, 3,5-dimethoxy-4-hydroxycinnamaldehyde, 2-phenyl-3-(2-furyl)prop-2-enal, ethyl vanillin acetate, vanillin isobutyrate, vanillin acetate, asaronaldehyde and mixtures thereof.

In another embodiment aldehydes may be selected from hexyl cinnamic aldehyde, 4-hydroxy-3-methoxycinnamaldehyde, decanal and mixtures thereof.

Other organic compounds suitable herein are compounds acting on nose receptors. The materials listed hereinafter inhibit the receptors of the nose, hereinafter called "nose blocking". When used, these materials may significantly reduce the capability for the nose to detect the malodours. The nose blocking is possible due to the volatile nature of the materials selected, which are evaporating out of the absorbent article and are then inhaled into the nose of an individual generally within somewhat close range of the article, e.g. within about 0 to 10 meters of the article (although this should in no way be intended to limit the scope of the invention) by normal breathing. The blocking of the nose receptors is of course only temporary. Suitable nose blocking materials include menthol, menthyl acetate, (5R)-2-methyl-5-prop-1-en-2-ylcyclohex-2-en-1-one, 3-methyl-4-(2,6,6-trimethyl-2-cyclohexen-1-yl)-3-buten-2-one, methyl dihydro jasmonate, hexyl-2-methyl butyrate, 4-(2,6,6-trimethylcyclohen-1-en-1-yl)but-3-en-2-one, 4-(2,6,6-trimethyl-1-cycloexen-1-yl)-3-buten-2-one, 3-buten-2-one, 4-(2,6,6-trimethyl-2-cyclohexen-1-yl)-, (E)-, menthyl lactate, isomenthyl acetate, isomenthyl propionate, isomenthyl isobutyrate, isomenthyl butyrate, camphor and p-menthane. The materials also include their isomeric forms, diastereomers and enantiomers. Advantageously, in generally, the above materials have only a very slight inherent odour but show a high degree of nose receptor blocking.

Other organic compounds which can be used in the present invention include limonene, eucalyptol, cresol, linalool, tetra-hydrolinalool, myrcenol, tetra hydromyrcenol, di-hydromyrcenol, myrcene, cytronellol, cytronellyil derivatives, geraniol, geranyl derivatives, linalyl acetate, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, benzylacetate, camphene, citronellal, di-hydrocumarin, di-hydromyrcenyl acetate, geraniol, geranial, encalyptus, isoamylacetate, ethyl, and/or triethyl acetate, para-cresol and para-cymene, benzyl-benzoate, isopropyl myristate, methyl abietate, ethanol, isopropanol, diethylene glycol monoethyl ether, glycerol, propylene glycol, 1,2-butylene glycol, dipropylene glycol, 2-methyl-2,4-pentanediol, diethyl phthalate, triethyl citrate, diethyl sebacate.

All the organic compounds mentioned above can be included in the odour control material alone or, more often as mixtures thereof.

Cyclodextrin Inclusion Complex

As used herein, the term "cyclodextrin" includes any of the known cyclodextrins such as substituted and unsubstituted cyclodextrins containing from about six to about twelve glucose units, for example alpha-cyclodextrin, beta-cyclodextrin, gamma-cyclodextrin and/or their derivatives and/or mixtures thereof. For example, the present invention may use cyclodextrins selected from the group consisting of beta-cyclodextrin, alpha-cyclodextrin, hydroxypropyl alpha-cyclodextrin, hydroxypropyl beta-cyclodextrin, methylated-alpha-cyclodextrin, methylated-beta-cyclodextrin, and mixtures thereof.

Cyclodextrin particles and cyclodextrin inclusion complexes of organic compounds can be formed by various methods which are well known in the art. An early reference is European Patent EP392608B1 from The Procter & Gamble Company which describes cyclodextrin inclusion complexes of organic compounds and their use in disposable absorbent articles.

For example, a solvent (e.g., water or an organic solvent suitable for the organic compound to be complexed), unloaded cyclodextrin particles, and the organic compound which need to be complexed can be placed into a container and then mixed for a period of time to permit loading of organic molecules into "cavities" of cyclodextrin molecules. The mixture may or may not be processed further; e.g., processed through a colloid mill and/or homogenizer. The solvent is then substantially removed from the resulting mixture or slurry to yield cyclodextrin complex particles, e.g. via spray drying. Different manufacturing techniques may however impart different particle/complex characterizations, which may or may not be desirable in the absorbent articles, depending on the specific usage and conditions. In some embodiments the particles of cyclodextrin inclusion complexes have a low level of moisture prior to their inclusion into the polysiloxane carrier, typically of less than about 20% by weight of the particles, or of less than about 10% by weight of the particles, or of less than about 6% by weight of the particles. Spray drying a slurry of inclusion complexes of cyclodextrin and organic compounds is one manufacturing technique capable of producing the cyclodextrin particles and cyclodextrin complexes having the above-noted, moisture levels. Cyclodextrin complexes can also be obtained using known techniques and an extrusion process (kneading) however the resulting material will in general contain a higher humidity and a lower complexation efficiency. WO2008/104960 from The Procter & Gamble Company provides a detailed overview of the most suitable techniques to prepare the cyclodextrin inclusion complexes.

Polysiloxane Oil.

According to the present invention the cyclodextrin inclusion complex is dispersed in a matrix comprising a polysiloxane oil. In some cases the cyclodextrin inclusion complex is dispersed in a matrix comprising more than 50% or more than 70% or more than 90% wt. of a polysiloxane oil (excluding the cyclodextrin inclusion complex) or is dispersed in a matrix consisting of polysiloxane oil. In all embodiments the polysiloxane oil can be polydimethilsiloxane (PDMS) or a polysiloxane polymer grafted with polyether (typically polyethylene oxide and or polypropylene oxide) chains such as those also called "silicone glycol copolymers" or "poly(oxyethylene. oxypropylene) methyl polisiloxane copolymer". Such materials are commercially available from Dow Corning and one suitable example is DC190. The presence of polyether chains grafted on the polysiloxane backbone may increase the hydrophilicity of the base polymer without impacting the release of the organic material from the inclusion complex, so that the more hydrophilic matrix allows better fluid movement and acquisition speed in the absorbent articles even in the presence of relatively high amounts of odour control material.

The polysiloxane oil dispersion of the cyclodextrin complex is in the form a low viscosity liquid which can be easily handled during the manufacturing of the absorbent articles and can be easily applied on the absorbent article at any stage of the manufacturing process.

An additional advantage of using a polysiloxane oil dispersion of the cyclodextrin complex is that the material can be easily applied in patterns on the desired surface as it will be described below when describing the patterns of application.

In general the weight ratio between the matrix comprising polysiloxane oil and the cyclodextrin inclusion complex is from 10:1 to 1:2. In some cases it can be from 5:1 to 1:1. In other cases it can be from 2:1 to 1:1. Higher amounts of cyclodextrin inclusion complex can make the material too pasty to be handled easily, while lower amounts can require a too large amount of matrix in order to deliver the right amount of cyclodextrin inclusion complex within the absorbent article.

As mentioned above, most organic compounds usable in odour control materials are volatile and tend to evaporate to some extent so that their amount in a commercial absorbent article is difficult to control. In order to preserve volatile compounds one successful route is to incorporate the volatile organic compounds into inclusion complexes of cyclodextrins. Such complexes release the complexed compound when triggered by the contact with humidity such as that which can be contained in bodily fluids. Without wishing to be bound by theory it is believed that the presence of water can weaken the chemical bonds among the cyclodextrin and the organic compound by forming hydrogen bonding with it. In some cases therefore the cyclodextrin inclusion complex must be protected from humidity which can be present in the air or can contact the absorbent article during its storage. The present invention provides a solution for protecting from humidity the cyclodextrin complex of an organic compound while at the same time allowing its easy and complete release when needed.

The specific selection of a polysiloxane oil has been surprisingly found to provide significant advantages because if more hydrophobic matrixes (such as mineral oil or petrolatum) are used the body fluids have less chances to enter in contact with the inclusion complex of cyclodextrine, while if more hydrophilic matrixes are used (such as PEG or glycerol), such matrixes can trigger the release of the complexed compound earlier than desired. A polysiloxane oil based matrix effectively protects the complex from moisture and at the same time allow prompt release when needed.

The advantages provided by the present invention will be present for any organic compound as all organic compounds suitable herein have a certain volatility, however the advantages will be more evident for organic compounds having a higher volatility so that the present invention is particularly suitable when the organic compound is selected from those having least a medium to high volatility.

In the present invention the volatility of organic compounds has been measured trough their Kovats Index. The Kovats index is a standard measurement performed in the perfume industry for the perfume raw materials and which in the present case has been applied to all the organic compounds of the present invention.

The Kovats Index of an organic compound is defined by the selective retention of the organic compound onto chromatographic columns. The values of the Kovats Index herein are obtained with a chromatographic column DB 5 (or equivalent), 30 m, 0.25 mm, 1.00 μm, operating under the following conditions: 50 300° C., 4° C./min, 12.0 psi, constant flow; DB 5 columns are e.g. available from Agilent Technologies Inc (formerly J&W Scientific), equivalent columns can be readily identified by the man skilled in the art using the commonly available equivalence tables. The value of the Kovats index for an organic compound is determined by its polarity, molecular weight, vapor pressure, boiling point, and the stationary phase property and is considered a good measure of its volatility.

For the purposes of the present invention are considered having a medium to high volatility those compounds having a Kovats index between 500 and 2000.

The absorbent articles being provided with the odour control material herein can be any kind of absorbent articles for personal hygiene known in the art. The odour control material of the present invention can be present in any part of the absorbent article. In some embodiments the odour control system can be applied on the wearer side of the topsheet, or on the garment side of the topsheet, or within the topsheet, or on the wearer side of the absorbent element, or on the garment side of the absorbent element, or within the absorbent element, or on the wearer side of the backsheet, or (if a secondary topsheet is present) on the wearer side of the secondary topsheet, or on the garment side of the secondary topsheet, or within the secondary topsheet, or (if an acquisition layer is present) on the wearer side of the acquisition layer, or on the garment side of the acquisition layer, or within the acquisition layer, or on any side of any other component of the absorbent article if present such as core wrap, further plastic foam or nonwoven layers, secondary backsheets or mixture thereof. The area of placement of the odour control material is usually in fluid communication with the area where bodily fluids enter the article.

In those embodiments where the odour control material is applied on the wearer side or the garment side of the absorbent element, or within the same absorbent element, or on a surface of another layer forming the article said surface being in immediate contact with the garment facing surface or the body facing surface of the absorbent element, the odour control material might be more effective because this configuration allows more intimate and more prolonged contact with the body fluids.

As mentioned, the odour control material can be introduced within or applied on any of the layers of the absorbent article. When it is applied on the surface of a layer it can be uniformly sprayed, but it is in general advantageous to apply the odour control material in patterns like spirals, serpentines, stripes, dots or any other patterned application known in the art. For example the odour control material can be applied using conventional glue application equipment such as slot applicator, which can be used for striped patterns, or air assisted applicators for patterned applications (like spray, spiral, serpentine, fibrils, Omega®, Signature® and the like) because this allow to position the odour control material in a way that it does not impact fluid acquisition (i.e. in a fem care article the material is not applied in correspondence with the vaginal opening) and anyway the pattern, having a large void space, allows fluid penetration also on the sides. Also patterned applications are helpful because it allows a precise application so that it is easier to avoid contact with the glue which connects the various layers of the article the article and which performance can be negatively affected by the contact with polysiloxane oil.

FIG. 1 shows an absorbent article according to the invention. FIG. 1b is a section of the same article along the line indicated by (i) in FIG. 1. The article (10) comprise a topsheet (20), a backsheet (30), an absorbent element (40), a secondary topsheet (50) and two spirals of odour control material (60) according to the invention applied on the absorbent core body facing surface.

The odour control material of the present invention can comprise other ingredients such as colorants, antioxidants, stabilizers, emulsifiers, surfactants, fillers, other uncomplexed perfumes and odour control materials selected among those mentioned in the present application or known in the art. In some embodiments the odour control material will comprise more than 50% or more than 80% or more than 95% or more than 99% wt. of the dispersion of cyclodextrine inclusion complex in polysiloxane oil. The odour control material will be in general introduced in absorbent articles at an amount of from 10 to 5000 mg per article, or from 20 to 1000 mg per article or from 30 to 500 mg per article or from 70 to 300 mg per article.

EXAMPLES

1. Preparation of the Odour Control Material

The following materials are added in order in a mildly agitated vessel, to create movement at the top of fluid, but without creating air bubbles.

55 g of distilled water, 41 g of beta cyclodextrine particles (contains nominally 12% moisture) 4 grams of a 50-50 wt % mixture of menthyl acetate and hexylcinnamic aldehyde. The slurry is agitated for 30 minutes and then passed through a colloid mill, (Gaulin mill). The rheology of the solution changes to a viscous slurry as the complexation occurs. The slurry is then dried via nozzle spray drying at an inlet temperature of approximately 195° C. and an outlet temperature of about 98° C. The result is a powder with moisture content of about 5% wt. and an organic molecule loading of about 8% wt.

2. Preparation of the Dispersion in PDMS

Grams of the inclusion complex prepared at point 1 are added slowly to 60 grams of PDMS in a mixer while stirring, obtaining an homogeneous dispersion which is kept under stirring.

3. Preparation of an Article

A sanitary napkin Always™ Regular as currently sold by The Procter & Gamble Company is opened by cutting the seal around the perimeter. The layers making up the article are separated, in particular the topsheet and the secondary topsheet while the assembly absorbent core/backsheet is left assembled. 170 mg of the dispersion prepared at point 2 are applied on the garment facing side of the secondary topsheet in two thin spirals similar to those shown in FIG. 1. The layers of the article are then re-assembled in their original order and orientation and a new thermal sealing is provided along the periphery.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it is alone, or in any combination with any other reference or references, teaches, suggests or discloses any such invention. Further, to the extend that any meaning or definition of term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a) a liquid permeable topsheet, a backsheet, and an absorbent element comprised between the topsheet and the backsheet, each of the topsheet, backsheet and absorbent element having a body facing side and a garment facing side; and
   b) an odour control material, said odour control material comprising at least one inclusion complex of cyclodextrin with an organic compound which is dispersed in a matrix comprising a polysiloxane oil;
   wherein the complexed cyclodextrin has less than 20% moisture by weight of the complexed cyclodextrin particles prior to their inclusion into the polysiloxane carrier.

2. An absorbent article according to claim 1 wherein the cyclodextrin is selected from α or β cyclodextrin.

3. An absorbent article according to claim 1 wherein the organic compound has a Kovats Index between 500 and 2000, said Kovats Index being measured with a chromatographic column DB 5, 30 m, 0.25 mm, 1.00 μm, operating at 50-300° C., 4° C./min, 12.0 psi, constant flow.

4. An absorbent article according to claim 1 wherein the odour control material is applied on the body facing side or on the garment facing side of the topsheet.

5. An absorbent article according to claim 1 wherein the odour control material is applied on the body facing side of the backsheet.

6. An absorbent article according to claim 1 wherein the odour control material is applied on the body facing side or on the garment facing side of or within the absorbent element.

7. An absorbent article according to claim 1 further comprising an additional layer of material positioned between the topsheet and the absorbent element wherein the odour control material is applied on the body facing side or on the garment facing side of said layer.

8. An absorbent article according to claim 1 further comprising an additional layer of material positioned between the absorbent element and the backsheet wherein the odour control material is applied on the body facing side or on the garment facing side of said layer.

9. An absorbent article according to claim 1, wherein the odour control material releases an organic compound upon being wetted.

10. An absorbent article comprising:
    a) a liquid permeable topsheet, a backsheet, and an absorbent element comprised between the topsheet and the backsheet, each of the topsheet, backsheet and absorbent element having a body facing side and a garment facing side; and
    b) an odour control material, said odour control material comprising at least one inclusion complex of cyclodextrin with an organic compound which is dispersed in a matrix comprising a polysiloxane oil;
    wherein the complexed cyclodextrin are solid particles in the polysiloxane oil; and
    wherein the complexed cyclodextrin has less than 20% moisture by weight of the complexed cyclodextrin particles prior to their inclusion into the polysiloxane carrier.

11. An absorbent article according to claim 10, wherein the cyclodextrin is selected from α or β cyclodextrin.

12. An absorbent article according to claim 10, wherein the odour control material releases an organic compound upon being wetted.

13. An absorbent article comprising:
    a) a liquid permeable topsheet, a backsheet, and an absorbent element comprised between the topsheet and the backsheet, each of the topsheet, backsheet and absorbent element having a body facing side and a garment facing side; and
    b) an odour control material, said odour control material comprising at least one inclusion complex of cyclodextrin with an organic compound which is dispersed in a matrix comprising a polysiloxane oil;
    wherein the complexed cyclodextrin are solid particles in the polysiloxane oil;
    wherein the complexed cyclodextrin has less than 20% moisture by weight of the complexed cyclodextrin particles prior to their inclusion into the polysiloxane carrier; and
    wherein the odour control material releases an organic compound upon being wetted.

* * * * *